United States Patent [19]

Mölls et al.

[11] Patent Number: 5,169,644
[45] Date of Patent: Dec. 8, 1992

[54] COMBINATION CARRIER GRANULES

[75] Inventors: Hans-Heinz Mölls, Herborn; Jörn Schrader, Monheim; Edmund Krauthausen, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 668,371

[22] Filed: Mar. 11, 1991

Related U.S. Application Data

[63] Continuation of Ser. No. 283,040, Dec. 5, 1988, abandoned, which is a continuation of Ser. No. 826,429, Feb. 5, 1986, abandoned.

[30] Foreign Application Priority Data

Feb. 16, 1985 [DE] Fed. Rep. of Germany ....... 3505424

[51] Int. Cl.$^5$ ................................................ A61K 9/58
[52] U.S. Cl. ................................ 424/497; 514/772.2; 424/419
[58] Field of Search ................. 424/497, 419, 78; 514/772.2

[56] References Cited

U.S. PATENT DOCUMENTS 3,137,618  6/1964  Pearce ............................ 424/497 X
4,144,050  3/1979  Frensch et al. ...................... 424/78

FOREIGN PATENT DOCUMENTS 2939746   8/1980  Fed. Rep. of Germany .
59-139306 8/1984  Japan .................................... 424/421
1015933   1/1966  United Kingdom .
1305320   1/1973  United Kingdom .

OTHER PUBLICATIONS

Chemical Patents Index, Basic Abstracts Journal, Section C, Week C/13, 21. Mai 1980, Derwent Publications Ltd., London, GB; & JP-A-80 008 481 (Kumiai Chemical Industrie K.K.) *C 53, Nr. 23117 C/13*.
Chemical Abstracts, Band 101, Nr. 25, 17. Dec. 1984, Seite 274, Zusammenfassung Nr. 224833r, Columbus, Ohio, US; & CS-A-217 457 (E. Beska et al.) May 15, 1984, *Zusammenfassung*.

Primary Examiner—Thurman K. Page
Assistant Examiner—Peter F. Kulkosky
Attorney, Agent, or Firm—Sprung Horn Kramer & Woods

[57] ABSTRACT

New combination carrier granulars are disclosed which comprise a granular carrier material having a compact surface and having applied thereto at least one liquid biocidally active compound, at least one solid biocidally active compound, polyvinyl acetate and polyvinyl alcohol. These combination carrier granules exhibit unexpectedly better activity than prior art materials and have unexpectly high abrasion resistance.

10 Claims, No Drawings

COMBINATION CARRIER GRANULES

This application is a continuation, of application Ser. No. 283,040, filed Dec. 5, 1988, now abandoned which in turn is a continuation of Ser. No. 826,429 filed Feb. 5, 1986, now abandoned.

The present invention relates to new combination carrier granules which contain solid and liquid biocidally active compounds. The invention furthermore relates to a process for the preparation of the new combination carrier granules and their use.

Numerous carrier granules which contain solid or liquid biocidally active compounds on a granular carrier material are already known (see Büchel "Pflanzenschutz und Schädlingsbekämpfung" ("Plant protection and combating pests"), Georg Thieme Verlag, Stuttgart 1977, pages 198 and 199).

Carrier granules with solid active compounds can thus be prepared, for example, by fixing the active components, if appropriate mixed with additives, in finely divided form to the compact surface of the carrier material with the aid of adhesives. A disadvantage is, however, that liquid active compounds cannot be applied to carrier materials by this method since the known adhesives do not harden in the presence of liquid active compounds.

Carrier granules which contain liquid herbicidally active compounds can be prepared, for example, by impregnating porous or absorbent carrier materials with liquid active compounds or with solutions of liquid active compounds in suitable solvents, in each case, if appropriate, mixed with additives. Carrier granules containing both solid and liquid biocidally active compounds can indeed be prepared by impregnating porous or absorbent carrier materials with solutions of solid and liquid active compounds and, if appropriate, additives in suitable solvents if solvents of this type can be discovered. However, the properties of these granules are not always satisfactory. Amongst other things, in particular, blocking of the pores or capillaries of the carrier material frequently occurs due to the solid active compounds crystallizing out, so that the active components are not released in the desired manner at the place of use.

New combination carrier granules which contain granular carrier material with a compact surface, at least one solid biocidally active compound, at least one liquid biocidally active compound, polyvinyl acetate and polyvinyl alcohol and, if appropriate, additives, have now been found.

It has furthermore been found that the combination carrier granules according to the invention can be prepared by a process in which granular carrier material with a compact surface is sprayed with an aqueous dispersion of polyvinyl acetate and polyvinyl alcohol in a mixer and then sprayed with at least one solid biocidally active compound, at least one liquid biocidally active compound, if appropriate, additives and if appropriate, an aqueous dispersion of polyvinyl acetate and polyvinyl alcohol, and the granular products thus obtained are dried.

Finally, it has been found that the combination carrier granules according to the invention can be used for the most diverse purposes in agriculture and in horticulture depending on the active components contained therein.

It is to be described as extremely surprising that the combination carrier granules according to the invention exhibit a better activity than the previously known granules in which solid and liquid active compounds are absorbed in the form of a solution onto porous or absorbent carrier materials. It is also unexpected that the products according to the invention are stable under conditions in practice. On the basis of the known prior art, it was to be assumed, in fact, that carrier granules with liquid active compounds would necessarily have to contain porous or absorbent carrier materials.

The combination carrier granules according to the invention are distinguished by a number of advantages. Thus, problem-free joint application of solid and liquid biocidally active compounds is made possible by these products. The active components contained in these granules are furthermore released in the particular desired manner at their place of use. Moreover, the combination carrier granules according to the invention are products which are distinguished by a very high abrasion resistance.

The products according to the invention are called combination carrier granules in the present case since they contain solid and liquid biocidally active compounds in combination with one another.

All the customary granular carrier substances with a compact surface which are contained in such granules can be present as carrier materials in the combination carrier granules according to the invention. Calcite, dolomite and sand, such as, for example, quartz sand, are preferably suitable.

The average particle diameter of the carrier materials can be varied within a certain range. The average particle diameter is in general between 0.1 and 3 mm, preferably between 0.3 and 1 mm.

Biocidally active compounds in the present case are to be understood as all the active compounds which can usually be employed in plant protection. These include, preferably, insecticides, acaricides, nematicides, fungicides, herbicides and plant growth regulators.

The granules according to the invention contain at least one biocidally active compound which is solid at room temperature and at least one biocidally active compound which is liquid at room temperature.

Carbamates can preferably be used as biocidally active compounds which are solid at room temperature. Examples which may be mentioned are: 2-isopropoxyphenyl N-methyl-carbamate, 2,3-dihydro-2,2-dimethyl-7-benzofuranyl N-methyl-carbamate, (3,5-dimethyl-4-methylthio-phenyl) N-methyl-carbamate and (naphthyl-1-yl) N-methyl-carbamate.

Phosphoric acid derivatives are preferably suitable as biocidally active compounds which are liquid at room temperature. Examples which may be mentioned are: O,O-diethyl O-(4-nitro-phenyl) thionophosphate, O,O-dimethyl O-(4-nitrophenyl) thionophosphate, O-ethyl O-(4-methylthio-phenyl) S-propyl dithiophosphate, (O,O-diethyl-thionophosphoryl)-αoximino-phenylacetonitrile, O,O-diethyl O-(3-chloro-4-methyl-7-coumarinyl) thiophosphate, S-[1,2-bis-(ethoxycarbonyl)-ethyl] O,O-dimethyl dithiophosphate, O,O-dimethyl O-(4-methylmercapto-3-methyl-phenyl) thionophosphate and O-ethyl-O-(2-isopropoxycarbonyl-phenyl) N-isopropyl-thionophosphoric acid ester-amide.

A mixture of polyvinyl acetate and polyvinyl alcohol functions as the binder in the combination carrier granules according to the invention.

Possible additives which can be present in the combination carrier granules according to the invention are extenders, grinding auxiliaries, dyestuffs, water and organic solvents.

Preferred possible extenders here are fine-grained inorganic solids, such as natural rock powders, for example kaolins, aluminas, talc, chalk, quartz powder, attapulgite, montmorillonite, sepiolith or diatomaceous earth, and furthermore synthetic rock powders, such as highly disperse silica.

Possible grinding auxiliaries are all the substances which can usually be employed for this purpose. Kaolins, aluminas, talc, chalk and quartz powder may be mentioned as preferred.

Dyestuffs which may be mentioned which are suitable as additives are inorganic pigments, such as iron oxide, titanium dioxide and Prussian blue, and organic dyestuffs, such as anthraquinone dyestuffs, azo dyestuffs and metal phthalocyanine dyestuffs.

Possible organic solvents are all the organic solvents which can usually be employed for the preparation of carrier granules. Preferred possible solvents are low-boiling organic solvents, such as methanol, ethanol, butanol and methylene chloride.

The granules according to the invention consist of granular carrier materials, on the compact surface of which is an enveloping layer containing at least one solid biocidally active compound and at least one liquid biocidally active compound as well as a mixture of polyvinyl acetate and polyvinyl alcohol, acting as a binder, and, if appropriate, additives. The components present in the enveloping layer can partly also penetrate into depressions in the carrier material.

The percentage contents of the components contained in the combination carrier granules according to the invention can be varied within substantial ranges. The content of carrier material is in general between 50 and 98% by weight, preferably between 60 and 92% by weight. The content of liquid and also of solid biocidally active compounds is in general between 0.1 and 20% by weight, preferably between 0.5 and 15% by weight. The content of the mixture of polyvinyl acetate and polyvinyl alcohol functioning as the binder is in general between 0.1 and 4% by weight, preferably between 0.3 and 3% by weight, in general 0.05 to 0.25 part by weight, preferably 0.1 to 0.2 part by weight, of polyvinyl alcohol being present per part of polyvinyl acetate. The granules contain additives, if appropriate, in amounts of 1 to 40 parts by weight, preferably 2 to 30 parts by weight.

All those components which have already been mentioned as preferred in connection with the description of the combination carrier granules according to the invention can preferably be used in the preparation of the combination carrier granules according to the invention.

It is necessary to employ the solid biocidally active compounds in finely divided form in the preparation of the granules according to the invention. For this, the biocidally active compounds which are solid at room temperature are in general used in the finely ground state, if appropriate mixed with grinding auxiliaries. The biocidally active compounds which are liquid at room temperature are in general used as a mixture with extenders, such as attapulgite, montmorillonite, sepiolith or highly disperse silica. However, it is also possible to employ a mixture of liquid and solid biocidally active compounds, if appropriate mixed with grinding auxiliaries, in the finely divided state.

The mixture of polyvinyl acetate and polyvinyl alcohol functioning as the binder (adhesive) is employed in the form of an aqueous dispersion. Possible diluents here are, in addition to water, also organic solvents, preferably low-boiling organic solvents, such as methanol, ethanol, butanol and methylene chloride.

In carrying out the process according to the invention, a procedure is in general followed in which granular carrier material with a compact surface is introduced into a mixer and sprayed, while mixing continuously, with an aqueous dispersion of polyvinyl acetate and polyvinyl alcohol and then either, in succession, at least one solid biocidal active compound, if appropriate mixed with additives, and at least one liquid biocidal active compound, if appropriate mixed with additives, are added, or a mixture of at least one solid biocidal active compound and at least one liquid biocidal active compound, if appropriate mixed with additives, is added, if appropriate the product is sprayed again with an aqueous dispersion of polyvinyl acetate and polyvinyl alcohol, and the granular products thus obtained are dried.

The sequence in which the components are applied to the carrier material can be varied in the particular manner desired.

The process according to the invention is in general carried out at room temperature. However, it is also possible to carry out the process at a somewhat elevated temperature.

The drying temperature can be varied within a substantial range. In general, drying is carried out at granule temperatures of between 20° C. and 70° C., preferably between 30° C. and 65° C. If appropriate, drying can be carried out under reduced pressure. Drying can furthermore be carried out either in the mixer used to coat the carrier material or in a separate drying apparatus.

The process according to the invention can be carried out either batchwise or continuously in customary apparatuses.

The combination carrier granules according to the invention can be employed for the most diverse purposes, depending on the active components contained therein. Thus, they can be used, for example, for combating animal pests, fungi and/or weeds. If they contain plant growth regulators, they can also be employed for influencing the growth of crop plants.

The combination carrier granules according to the invention can be applied by customary methods, such as, for example, scattering.

The preparation of the combination carrier granules according to the invention can be seen from the following examples.

Preparation Examples

Comparison Example 176.94 g of quartz sand granules with a diameter of 0.4 to 0.8 mm are sprayed in a mixer, while continuously mixing at room temperature, with an aqueous dispersion containing 1.6 g of polyvinyl acetate. Thereafter, 13.86 g of a commercially available finely ground pulverulent mixture containing 10.47 g of 2,3-dihydro-2,2-dimethyl-7-benzofuranyl N-methyl-carbamate of the formula

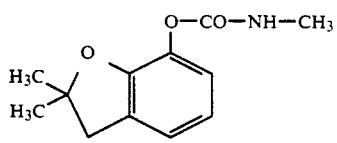

and 0.6 g of blue dyestuff and 7 g of a mixture consisting to the extent of 65.21 per cent by weight of O-ethyl O-(2-isopropoxycarbonyl-phenyl) N-isopropyl-thionophosphoric acid ester-amide of the formula

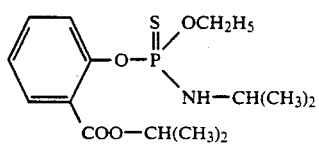

and to the extent of 34.79 per cent by weight of highly disperse silica, are added at room temperature. The components are mixed at room temperature for a further 10 minutes and then dried in the mixer at a maximum temperature of the material to be dried of 60° C. 200 g of combination carrier granules containing 5.2 per cent by weight of active compound of the formula (1) and 2.1 per cent by weight of active compound of the formula (2) are obtained in this manner.

The resulting granules exhibited severe abrasion and softening, so that they were unsuitable for use in practice.

Example 1

88.8 kg of quartz sand granules with a diameter of 0.3 to 0.7 mm are sprayed in a mixer, whilst mixing continuously at room temperature, with 3.34 kg of an aqueous dispersion containing 0.8 kg of polyvinyl acetate and 0.1 kg of polyvinyl alcohol. Thereafter, 6.62 kg of a commercially available finely ground pulverulent mixture containing 5 kg of 2,3-dihydro-2,2-dimethyl-7-benzofuranyl N-methyl-carbamate of the formula

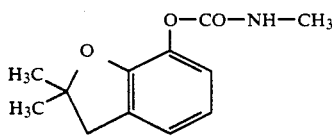

and a mixture of 2 kg of O-ethyl O-(2-isopropoxycarbonylphenyl) N-isopropylthionophosphoric acid ester-amide of the formula

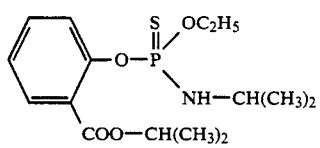

are added at room temperature to 0.37 kg of blue dyestuff and 0.37 kg of highly disperse silica. The components are mixed at room temperature for a further 10 minutes and then dried in the mixer at a maximum temperature of the material to be dried of 60° C. 100 kg of combination carrier granules containing 5% by weight of active compound of the formula (1) and 2% by weight of active compound of the formula (2) are obtained in this manner.

The granules are distinguished by a high abrasion resistance.

EXAMPLE 2

90.1 kg of quartz sand granules with a diameter of 0.3 to 0.7 mm are sprayed in a mixer, while continuously mixing at room temperature, with 3.34 kg of an aqueous dispersion containing 0.75 kg of polyvinyl acetate and 0.15 kg of polyvinyl alcohol. Thereafter, 5.3 kg of a commercially available finely ground pulverulent mixture containing 4 kg of 2,3-dihydro-2,2-dimethyl-7-benzofuranyl N-methyl-carbamate of the formula

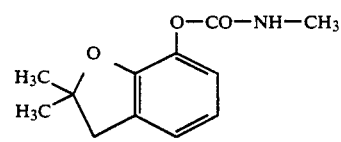

and a mixture of 2 kg of O-ethyl O-(2-isopropoxycarbonylphenyl) N-isopropylthionophosphoric acid ester-amide of the formula

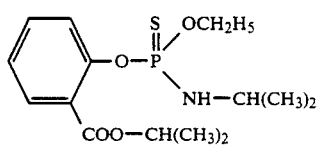

are added at room temperature to 0.37 kg of blue dyestuff and 1.34 kg of highly disperse silica. The components are mixed at room temperature for a further 10 minutes and then dried in the mixer at a maximum temperature of the material to be dried of 60° C. 100 kg of combination carrier granules containing 4% by weight of active compound of the formula (1) and 2% by weight of active compound of the formula (2) are obtained in this manner.

The granules are distinguished by a high abrasion resistance.

What is claimed is:

1. A combination carrier granule, which comprises a granular carrier material with a compact surface selected from the group consisting of natural and synthetic rock powders, at least one solid biocidally active compound, at least one liquid biocidally active compound, polyvinyl acetate, and polyvinyl acetate, said combination carrier granule being prepared by spraying said granular carrier material with an aqueous dispersion of polyvinyl acetate and polyvinyl alcohol in a mixer and then spraying with at least one solid biocidally active compound and at least one liquid biocidally active compound and then drying the granular product thus obtained, the dried granular product having improved abrasion resistance as compared to the same granular product not containing polyvinyl alcohol, and the dried granular product containing about 0.1 to about 4% by weight polyvinyl alcohol and polyvinyl acetate in a ratio of about 0.05 to about 0.25 parts by weight of polyvinyl alcohol per part of polyvinyl acetate.

2. The combination carrier granule according to claim 1, wherein the granular carrier material with a compact surface is selected from the group consisting of calcite, dolomite, and sand.

3. A combination carrier granule according to claim 1, wherein said solid biocidally active compound is a carbamate.

4. A combination carrier granule according to claim 1, wherein said liquid biocidally active compound is a phosphoric acid derivative.

5. A combination carrier granule according to claim 1, wherein said solid biocidally active compound is 2,3-dinydro-2,2-dimethyl-7-benzofuranyl N-methyl-carbamate.

6. A combination carrier granule according to claim 1, wherein said liquid biocidally active compound is O-ethyl O-(2-isopropoxycarbonylphenyl) N-isopropylthionophosphoric acid esteramide.

7. A combination carrier granule according to claim 1, comprising 0.1 to 20% by weight of said biocidally active compounds.

8. A combination carrier granule according to claim 1, wherein said suitable additive is selected from an extender, grinding auxiliary, dyestuff, water and/or an organic solvent.

9. A method of applying liquid and solid biocidally active compounds to plants and/or their environment comprising applying to said plants and/or their environment the combination carrier granules according to claim 1.

10. A combination carrier granule according to claim 1 comprising 50 to 98% by weight of said granular carrier material and 0.1 to 4% by weight of polyvinylacetate and polyvinyl alcohol.

* * * * *